United States Patent [19]

Georgiev et al.

[11] Patent Number: 4,774,334
[45] Date of Patent: Sep. 27, 1988

[54] FURANCARBOXAMIDES

[75] Inventors: Vassil S. Georgiev, Penfield; Thomas R. DeCory, Rochester, both of N.Y.

[73] Assignee: Pennwalt Corporation, Philadelphia, Pa.

[21] Appl. No.: 118,124

[22] Filed: Nov. 9, 1987

[51] Int. Cl.$^4$ .................. C07D 401/04; C07D 405/04; C07D 307/68; C07D 413/04
[52] U.S. Cl. .................................... 544/152; 546/165; 546/214; 548/517; 549/321
[58] Field of Search ................ 544/152; 546/214, 165; 548/517; 549/321

[56] References Cited

U.S. PATENT DOCUMENTS 4,625,040 11/1986 Georgiev et al. ................... 549/321

Primary Examiner—Robert W. Ramsuer

[57] ABSTRACT

Compounds possessing antiallergy activity have the formula:

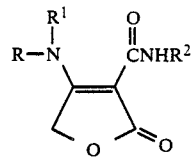

wherein R and $R^1$ are independently hydrogen or alkyl, or R and $R^1$ together with the attached nitrogen form a heterocyclic ring system selected from the group consisting of piperidinyl, pyrrolidinyl, morpholinyl and 1, 2, 3, 4-tetrohydroquinolinyl, and $R^2$ is phenyl or phenyl monosubstituted with a lower alkyl, a nitro, a halogenated methyl, a halogen or a lower alkoxy group.

20 Claims, No Drawings

FURANCARBOXAMIDES

BACKGROUND OF THE INVENTION

This invention relates generally to lactone derivatives of 2,5-dihydrofurans and more specifically to N-phenyl-2,5-dihydro-2-oxo-4-[(heterocyclyl) or (alkyl)amino]-3-furancarboxamides which have antiallergic properties. U.S. Pat. No. 4,625,040 issued Nov. 25, 1986, disclosed N-phenyl-2,5-dihydro-2-oxo-4-phenylamino-3-furancarboxamides and derivatives thereof with antiallergic properties.

SUMMARY OF THE INVENTION

In accordance with this invention there are provided compounds of the formula:

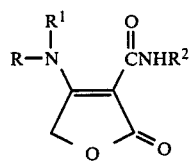

V wherein R and $R^1$ are independently hydrogen or alkyl, or R and $R^1$ together with the attached nitrogen form a heterocyclic ring system selected from the group consisting of piperidinyl, pyrrolidinyl, morpholinyl and 1,2,3,4-tetrahydroquinolinyl, and $R^2$ is phenyl or phenyl monosubstituted with a lower alkyl, a nitro, a halogenated methyl, a halogen or a lower alkoxy group.

DETAILED DESCRIPTION OF THE INVENTION

The N-phenyl-2,5-dihydro-2-oxo-4-[(heterocyclyl) or (alkyl)amine]-3-furancarboxamides of this invention having the above formula possess antiallergic properties.

The "lower alkyl" and "lower alkoxy" substituents mentioned above are straight or branched chain saturated hydrocarbon groups having from 1 to 4 carbon atoms including, for example, methyl, ethyl, propyl, isopropyl, butyl and isobutyl groups. The "alkyl" radicals mentioned above are likewise straight or branched chain saturated hydrocarbon groups, but these contain from 1 to 18 carbon atoms. For example, the "alkyl" groups are those recited for "lower alkyl" and additionally include, e.g., pentyl, octyl, isooctyl, decyl, dodecyl, hexadecyl, octadecyl and isooctadecyl groups. As used herein, "halogen" refers to chlorine, fluorine, bromine and iodine but the preferred halogen is chlorine.

The compounds V of this invention can be prepared according to the following diagram by an initial base-catalyzed cyclocondensation of ethyl 4-chloroacetate I with an appropriate isocyanate derivative II. The resulting 3(2H)-furanone compound III is hydrolyzed under alkaline condition to give the corresponding carboxylic acid IV, which in turn is treated with one equivalent of an appropriate amine (or N-heterocycle) in the presence of triethylamine and bis(2-oxo-3-oxazolidinyl)phosphinic chloride (BOP-Cl) to provide the 5(2H)-furanone V by a rearrangement.

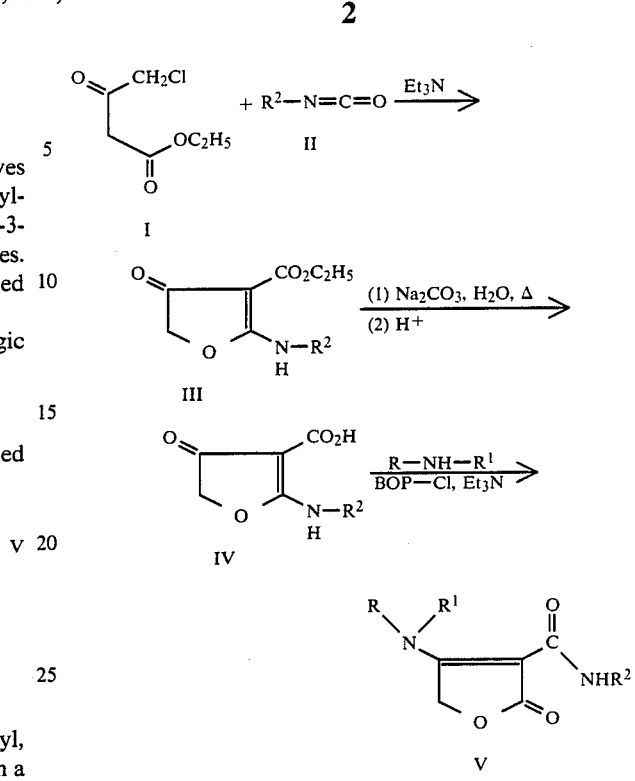

METHOD OF TESTING

The compounds of the invention are tested for antiallergy activity in the rat dermal vascular permeability test. In this test, groups of ten male rats are intraperitoneally or perorally administered either the test compound, at a dosage of 100 mg/kg of rat weight as a 0.85% solution in saline, or the positive reference standard cyproheptadine (1 mg/kg) one hour prior to an intravenous injection of 1 ml of a 0.5% solution of Evan's blue dye into naive animals. Ten minutes later the animals are challenged by intradermally injecting 0.1 ml of a solution of either serotonin (1 μg/ml), histamine (20 μg/ml) or bradykinin (10 μg/ml) into separate sites on the back. Five minutes following challange the animals are killed, the skin retracted, and the mean diameter of the blue wheal and flare reactions determined. The percent inhibition of the wheal reaction is calculated as the difference in diameter between the saline control and drug treated groups divided by the control diameter times 100. Statistical analysis of the data is done using the poolt program. According to this test Example 3(a) produced antiallergy activities of 23.8% and 29.7% inhibition with respect to serotonin and bradykinin respectively. The invention is further illustrated by, but is not intended to be limited to, the following examples which describe the preparation of a number of compounds of the invention.

EXAMPLE 1

Preparation of N-Phenyl-4-tetradecylamino-2,5-dihydro-2-oxo-3-furancarboxamide [V,R=CH₃(CH₂)₁₃, $R^1$=H, $R^2$=C₆H₅]

Under a nitrogen atmosphere, a solution of triethylamine (3.50 ml, 0.025 mol) in 20 ml of methylene dichloride was added dropwise to a solution of 2-anilino-4-oxo-3-furoic acid (5.0 g, 0.023 mol) in 40 ml of methylene dichloride, at 0°–5° C. (ice water bath). Then, BOP-Cl (5.80 g, 0.023 mol) was added in one portion and the reaction mixture was stirred at 0°–5° C. for 40 min, followed by a dropwise addition (over a 6-hour period) of a solution of 1-tetradecylamine (5.80 g, 0.025 mol) in 200 ml of methylene dichloride. The reaction mixture was allowed to warm up to ambient temperature and was stirred for 18 hours, then poured into ice water and extracted with methylene dichloride. The organic extract was washed sequentially with water and 5% aqueous solution of sodium bicarbonate, dried over anhydrous magnesium sulfate and the solvent evaporated under reduced pressure. The resulting crude product was flash-chromatographed over silica gel (using chloroform as eluant) to provide pure compound V [R=CH$_3$(CH$_2$)$_{13}$, R$^1$=H, R$^2$=C$_6$H$_5$]. Yield: 1.37 g, m.p. 84°–85° C. (ethanol). Anal. Calcd. for C$_{25}$H$_{38}$N$_2$O$_3$: C, 72.43; H, 9.24; N, 6.76. Found: C, 72.51; H, 9.32; N, 6.66.

EXAMPLE 2

Preparation of
N-Phenyl-4-(1,2,3,4-tetrahydroquinolin-1yl)-2,5-dihydro-2-oxo-3-furancarboxamide (V, RNR$^1$=1,2,3,4-tetrahydroquinolin-1yl, R$^2$=C$_6$H$_5$)

Under a nitrogen atmosphere, a solution of triethylamine (14.0 ml, 0.10 mol) in 40 ml of methylene dichloride was added dropwise to a solution of 2-anilino-4-oxo-3-furoic acid (10.0 g, 0.046 mol) in 80 ml of methylene dichloride, at 0°–5° C. (ice water bath). Then BOP-Cl (11.60 g, 0.046 mol) was added in one portion at 0°–5° C. and the reaction mixture was stirred at 0°–5° C. for 45 min, followed by the dropwise addition (over a 6-hour period) of a solution of 1,2,3,4-tetrahydroquinoline (6.40 ml, 0.051 mol) in 100 ml of methylene dichloride. The reaction mixture was allowed to warm up to ambient temperature and was stirred for an additional 18 hours, then poured into ice water and extracted with methylene dichloride. The combined organic extract was washed sequentially with water and 5% aquous solution of sodium bicarbonate, dried over anhydrous magnesium sulfate and the solvent evaporated under reduced pressure to provide crude compound V (RNR$^1$=1,2,3,4-tetrahydroquinolin-1-yl, R$^2$=C$_6$H$_5$) which was recrystallized from ethanol. Yield: 4.3 g, m.p. 155°–157° C. Anal. Calcd. for C$_{20}$H$_{18}$N$_2$O$_3$: C, 71,84; H, 5.43; N, 8.38. Found: 71.62; H, 5.52; N, 8.37.

EXAMPLE 3

The following compounds were prepared by procedures similar to that of Example 2 by using the appropriate N-heterocycle and a furoic acid intermediate:

(a) N-Phenyl-4-(morpholin-4-yl)-2,5-dihydro-2-oxo-3-furancarboxamide
(V, RNR$^1$=morpholin-4-yl, R$^2$=C$_6$H$_5$), m.p. 205°–206.5° C. (ethanol). Anal. Calcd. for C$_{15}$H$_{16}$N$_2$O$_3$: C, 62.71; H, 5.26; N, 9.75. Found: C, 62.59; H, 5.76; N, 9.74;

(b) N-Phenyl-4-(piperidin-1-yl)-2,5-dihydro-2-oxo-3-furancarboxamide
(V, RNR$^1$=piperidin-1-yl, R$^2$=C$_6$H$_5$), m.p. 157°–158° C. (ethanol). Anal. Calcd. for C$_{16}$H$_{18}$N$_2$O$_3$: C, 67.12; H, 6.34; N, 9.78. Found: C, 67.08; H, 6.47; N, 9.77.

(c) N-Phenyl-4-(pyrrolidin-1-yl)-2,5-dihydro-2-oxo-3-furancarboxamide (V, RNR$^1$=pyrrolidin-1-yl, R$^2$=C$_6$H$_5$), m.p. 200°–201° C. (ethanol).
Anal. Calcd. for C$_{15}$H$_{16}$N$_2$O$_3$; C, 66.16; H, 5.92; N, 10.29. Found: C, 66.14; H, 5.97; N, 10.27

EXAMPLE 4

The N-phenyl-4-(N,N-diethylamino)-2,5-dihydro-2-oxo-3-furancarboxamide (V, R=R$^1$=C$_2$H$_5$, R$^2$=C$_6$H$_5$) was prepared by a procedure similar to that of Example 2 by using N,N-diethylamine in place of 1-tetradecylamine. Compound IV (R=R$^1$C$_2$H$_5$, R$^2$=C$_6$H$_5$) was found to have a boiling point of 195°–200° C. (0.015 mmHg). Anal. Calcd. for C$_{15}$H$_{18}$N$_2$O$_3$.xH$_2$O: C, 64.62; H, 6.69; N, 10.05. Found: C, 64.74; H, 7.06; N, 10.05.

EXAMPLE 5

Various N-(substituted phenyl)-4-[(heterocyclyl) or (alkyl)amino]-2,5-dihydro-2-oxo-3-furancarboxamides V can be prepared according to the methods of Examples 2 and 3 or 1 and 4 respectively, by substituting for 2-anilino-4-oxo-3-furoic acid, the appropriate known 2-(substituted phenyl)amino-4-oxo-3-furoic acid.

For example
2-[(3-nitrophenyl)amino]-4-oxo-3-furoic acid
2-[(3-methoxyphenyl)amino]-4-oxo-3-furoic acid
2-[(4-bromophenyl)amino]-4-oxo-3-furoic acid
2-[(4-chlorophenyl)amino]-4-oxo-3-furoic acid
2-[[3-(trifluoromethyl)phenyl]amino]-4-oxo-3-furoic acid and
2-[(2-methylphenyl)amino]-4-oxo-3-furoic acid

We claim:
1. A compound of the formula:

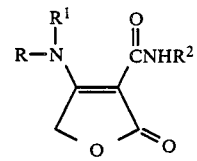

wherein the R and R$^1$ are independently hydrogen or alkyl, or R and R$^1$ together with the attached nitrogen form a heterocyclic ring system selected from the group consisting of piperidinyl, pyrrolidinyl, morpholinyl and 1,2,3,4-tetrahydroquinolinyl, and R$^2$ is phenyl or phenyl monosubstituted with a lower alkyl, a nitro, a halogenated methyl, a halogen or a lower alkoxy group.

2. The compound of claim 1 wherein r is an alkyl group having 1 to 18 carbon atoms, R$^1$ is hydrogen and R$^2$ is phenyl.

3. The compound of claim 1 wherein R and R$^1$ are lower alkyl groups, and R$^2$ is phenyl.

4. The compound of claim 1 wherein R and R$^1$ together with the attached nitrogen form a heterocyclic ring system selected from the group consisting of piperidinyl, pyrrolidinyl, morpholinyl and 1,2,3,4-tetrahydroquinolinyl.

5. The compound of claim 4 wherein the heterocyclic ring system is the 1,2,3,4-tetrahydroquinolinyl group.

6. The compound of claim 4 wherein the heterocyclic ring system is the piperidinyl group.

7. The compound of claim 4 wherein the heterocyclic ring system is the pyrrolidinyl group.

8. The compound of claim 4 wherein the heterocyclic ring system is the morpholinyl group.

9. The compound of claim 5 wherein R$^2$ is phenyl.
10. The compound of claim 6 wherein R$^2$ is phenyl.
11. The compound of claim 7 wherein R$^2$ is phenyl.

12. The compound of claim 8 wherein $R^2$ is phenyl.

13. The compound of claim 1 wherein $R^2$ is phenyl monosubstituted with a lower alkyl, a nitro, a halogenated methyl, a halogen or a lower alkoxy group.

14. The compound of claim 13 wherein said phenyl is substituted with a methyl group in the 2 position.

15. The compound of claim 13 wherein said phenyl is substituted with a nitro group in the 3 position.

16. The compound of claim 13 wherein said phenyl is substituted with chlorine in the 4 position.

17. The compound of claim 13 wherein said phenyl is substituted with a methoxy group in the 3 position.

18. The compound of claim 13 wherein said phenyl is substituted with a trifluoromethyl group in the 3 position.

19. The compound of claim 2 wherein said alkyl group is tetradecyl.

20. The compound of claim 3 wherein R and $R^1$ are methyl groups.

* * * * *

UNITED STATES PATENT AND TRADEMARK OFFICE
CERTIFICATE OF CORRECTION

PATENT NO. : 4,774,334

DATED : September 27, 1988

INVENTOR(S) : Vassil S. Georgiev, Thomas R. DeCory, Robert Allan Mack

It is certified that error appears in the above—identified patent and that said Letters Patent is hereby corrected as shown below:

On the title page,

Inventors: Vassil S. Georgiev, Penfield; Thomas R. DeCory, Rochester, both of N.Y.

should read

Inventors: Vassil S. Georgiev, Penfield; Thomas R. DeCory, Rochester; Robert A. Mack, Rochester; all of N.Y.

Signed and Sealed this

Twenty-eighth Day of February, 1989

Attest:

DONALD J. QUIGG

Attesting Officer

Commissioner of Patents and Trademarks